United States Patent [19]

Barrett

[11] Patent Number: 4,684,370
[45] Date of Patent: Aug. 4, 1987

[54] STENTS FOR BONE AUGMENTATION BY SURGICAL IMPLANT

[76] Inventor: Garret D. Barrett, Box 51-6357 Saginaw, Grand Blanc, Mich. 48439

[21] Appl. No.: 782,956

[22] Filed: Oct. 2, 1985

[51] Int. Cl.⁴ .............................................. A61F 2/00
[52] U.S. Cl. ..................................... 623/66; 623/16; 433/229
[58] Field of Search .......................... 623/11; 433/214; 433/214, 213, 171, 229, 66, 16

[56] References Cited

U.S. PATENT DOCUMENTS

| | | | |
|---|---|---|---|
| 3,577,640 | 5/1971 | Lee | 433/214 X |
| 3,787,900 | 1/1974 | McGee | 623/16 |
| 3,913,229 | 10/1975 | Driskell et al. | 623/16 X |
| 4,097,935 | 7/1978 | Jarcho | 623/16 |
| 4,277,238 | 7/1981 | Katagiri | 623/16 X |
| 4,468,202 | 8/1984 | Cohen | 433/214 X |

Primary Examiner—Richard J. Apley
Assistant Examiner—Alan W. Cannon
Attorney, Agent, or Firm—John R. Benefiel

[57] ABSTRACT

Stents are disclosed for use in surgical augmentation of tissue at body sites such as the alveolar ridge, by the use of an implant material, i.e., hydroxylapatite (HA) for example. The stents are used for surgical positioning and shaping of the implant material and for post operative maintenance thereof. The stents are constructed of a transparent substance, molded to a model of specific desired tissue morphology and adjacent tissues. In use, a stent is positioned to define a confining open sided cavity corresponding to the specific predetermined tissue morphology. Implant material is injected or placed beneath the soft tissue over which the stent is positioned, to expand the tissue to occupy entirely the inside of the stent cavity, this step facilitated by observation through the transparent stent walls. A series of modified versions of the stents are typically employed for alveolar ridge augmentation, including stents having different relief openings for surgical access to anterior and posterior ridge sections. An unrelieved stent is used for checking final ridge morphology, and may be ligated in place to insure proper post operative bonding and securement of the implant.

9 Claims, 8 Drawing Figures

STENTS FOR BONE AUGMENTATION BY SURGICAL IMPLANT

BACKGROUND OF THE INVENTION

The present invention is concerned with body tissue augmentation, and particularly with a stent for use in bone augmentation to restore the alveolar ridge by surgical implacement of implant material, i.e., granular or block hydroxylapatite (HA).

DESCRIPTION OF THE PRIOR ART

Persons who have lost their natural teeth may be fitted with a conventional upper and/or lower denture prosthesis in order fit to the upper or lower residual alveolar ridge. For various reasons the underlying bone mass supporting the ridge can be lost to the point that the residual alveolar ridge is inadequate for proper fitting of a denture prosthesis.

There has been heretofore been developed various surgical implant techniques for augmentation of bone, as for example the basal mandibular (lower) or maxilia (upper) bone structure underlying the alveolar ridge in order to surgically restore the tissue contours to a proper morphology.

HA is one very useful implant material that has been heretofore employed in such applications. It will bond and become ossified like to the natural bone if contact is maintained over a period of time to thereby enable augmenting of the alveolar ridge for the purposes described.

Difficulties are encountered in surgical implementation of this method in that the implant material is difficult to accurately shape and locate and to maintain in proper shape and location to insure an acceptable pre and post operative surgical ridge morphology.

Other difficulties also have been encountered including but not limited to migration of the implant material out of position, interarch space impingement, irregular postoperative arch morphology, delayed or deficient post bonding, dehiscence, soft tissue inflammation, and undesirable position of the HA material in relation to the residual osseous ridge.

Accordingly, it is an object of the present invention to provide surgical stents for use in such alveolar ridge augmentation which insures proper positioning and maintaining of desired morphology of the HA material, both during surgical placement and postoperatively, to alleviate the above described difficulties and complications.

SUMMARY OF THE INVENTION

These and other objects of the present invention which will become apparent upon a reading of the following specification and claims are achieved by a surgical stent fabricated by initially constructing a specific model of specific pre surgical morphological design as of the alveolar ridge, and adjacent oral soft tissues, by adding shapable material such as wax to a casting of the existing tissue morphology. The working model is thereafter augmented with permanent moldable material to create a master model of the desired ridge morphology. A stent is constructed from the master model by molding a thin sheet of transparent material such as polyvinyl acrylic into the morphology of the augmented master model.

The transparent stent member created has a section defining an open sided cavity corresponding to the desired ridge morphology, with adjacent flange portions for positioning the stent to properly position the cavity in the correct location by locating on the adjacent soft tissues.

A series of the stents are used, each relieved for access to the anterior and posterior sections of the ridge, and unrelieved versions for confirming the ridge morphology after surgery, and to be ligated for temporary post operative implacement during implant material bonding.

The implant procedure involves initially separating the soft tissue and periosteum from the residual osseous ridge using the stents as guides, by means of a tunneling or like surgical technique, progressing from vertical incisions located at the sites of the relieved areas on the stents. The implant material is then injected or positioned under the tissue successively in each section of the ridge to expand the tissue into contact with the cavity section of each stent. The predetermined morphology is completed by viewing through the transparent stent cavity sections, until complete stent cavity void is filled to conform to the stent morphology.

One or more unrelieved stents may then be used to check the augmented ridge morphology. This or another specific stent may be ligated into position for temporary postoperative implacement as indicated.

DETAILED DESCRIPTION

In the following detailed description, certain specific terminology will be employed for the sake of clarity and a particular embodiment described in accordance with the requirements of 35 USC 112, but it is to be understood that the same is not intended to be limiting and should not be so construed inasmuch as the invention is capable of taking many forms and variations within the scope of the appended claims.

According to the above described concept of the present invention, the stent consists of a molded member of transparent material such as polyacrylic plastic or other suitable materials, and having defined therein a cavity configured according to the restored tissue morphology, such as the alveolar ridge morphology, with adjacent flange portions such as to properly locate and position the stent within the patient's oral cavity.

Figure 1:
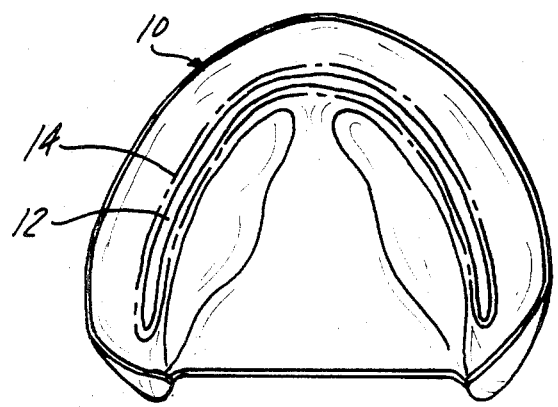
FIG. 1, is a plan view of a model of a residual alveolar ridge and adjacent oral tissues.
Figure 2:
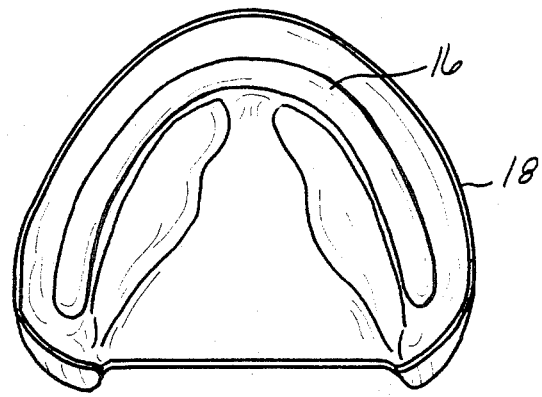
FIG. 2, is a plan view of an augmented working model with a desired alveolar ridge morphology.

Such a member is formed by initially creating a model 10 of the patient's residual alveolar ridge and adjacent oral tissues, as shown in FIG. 1, indicated at 12. Such model can be created by suitable conventional dental techniques such as obtaining an impression with the use of a tray and a mass of impression material, i.e., irreversible hydrocolloid, and immediately pouring a model using a proper mix of dental stone under vacuum.

From the casting 10 so produced, an augmented working model is prepared in which material is added to the residual ridge in the form of a mass of a shapable material such as wax, to create a model of a specific ridge morphology.

Such specific morphology is determined and formed from a study of the jaw relation records, examination of the working model mounted within an articulator, and intended design of the final prosthesis.

As a first step, the positioning of the augmentation mass relative to the residual ridge is marked in outline 14 on the model 10 such as to properly locate the augmentation mass with respect to the residual osseous ridge. After applying a sticky wax within the outline 14, a mass of hard baseplate wax or like material 16 is shaped over the outline 14 into the specific ridge morphology and design. The augmentation should not extend into any natural stress bearing area such as the buccal shelf.

After creating the augmented working model 18, the resultant working model of the desired ridge morphology should be evaluated as on an articulator for proper height, contour, width, and position relation to the anatomic residual ridge and specific prosthesis design.

Proper interarch distance and protrusive clearance may be confirmed with an opposing diagnostic wax rim set-up of teeth or an existing modified denture.

Figure 3:
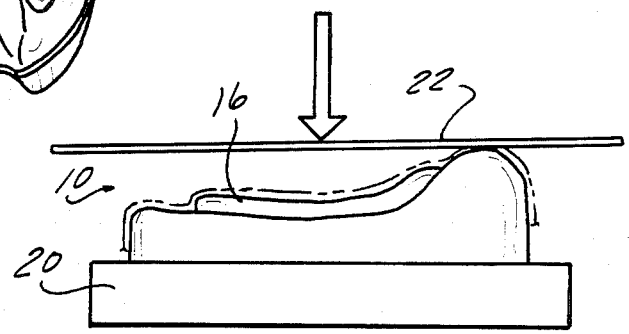
FIG. 3, is a diagrammatic representation of a vacuum molding of a stent according to the present invention using the augmented master model shown in FIG. 2.

The augmented working model 18 is then refrigerated in order to harden the wax ridge 16. After applying a thin film of petroleum jelly or suitable other lubricant over the working model and wax ridge 16, the stent 24 according to the present invention is formed by suitable vacuum forming or like techniques represented diagrammatically in FIG. 3.

In this method, the chilled augmented working model 18 is positioned on a vacuum platform 20 with a sheet 22 of clear plastic, such as 0.08 inch thick polyacrylic resin, to be drawn down over the model contours while applying minimal heat to reduce distortion of the chilled wax ridge 16 under the pressure of the molding process.

Figure 4:
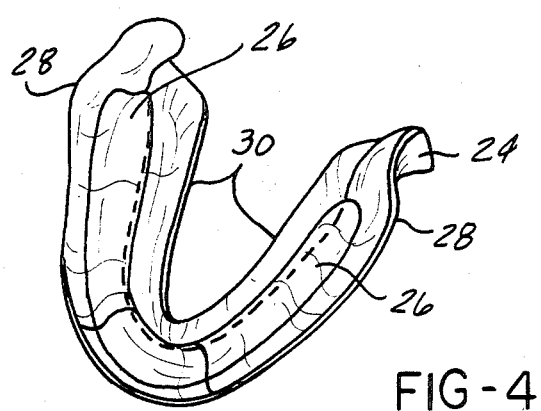
FIG. 4, is a perspective view of a stent according to the present invention.
Figure 5:
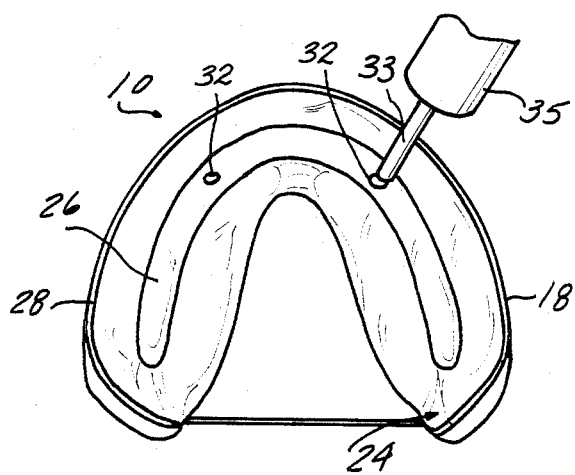
FIG. 5, is a plan view of a stent according to the present invention being used to create a permanent augmented master model of the restored alveolar ridge.

The plastic sheet 22 extends beyond the ridge 16 such that upon molding, as shown in FIG. 4, stent 24 is formed with a cavity section 26 defining an internal open sided cavity corresponding to the desired ridge morphology, as well as adjacent flange portions 28 and 30, corresponding to the adjacent oral tissues. Excess stent material extending beyond the perimeter of the model 18 is trimmed away.

Since the use of the stent 24 may involve three or more versions of the stent 24, repeated vacuum forming against an augmented "master" model is required.

Accordingly, the initial stent 24 is advantageously used to form the permanent augmented master model by providing a pair of access holes 32 in the stent 24, and stent 24 is replaced on the model 10 after removal of the wax ridge 16.

The quantity of wax removed is desirably placed into a syringe of the type to be used for HA implantation, so that the volume of implant material required may be referenced by the surgeon.

A plaster mix is injected into the access holes 32 by use of a monojet syringe 33 tip inserted into each access hole 32 as shown.

First, a thin coating of jelly is applied to the syringe barrel 35 and to the internal surface of the stent 24 in order to prevent adhesion of the plaster thereto; and to the peripheral borders outside the outlined intended augmentation.

Figure 6:
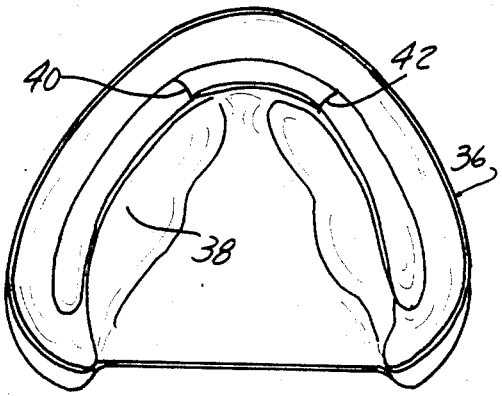
FIG. 6, is a plan view of the final master model of the restored alveolar ridge to specific preoperative morphology.
Figure 7:
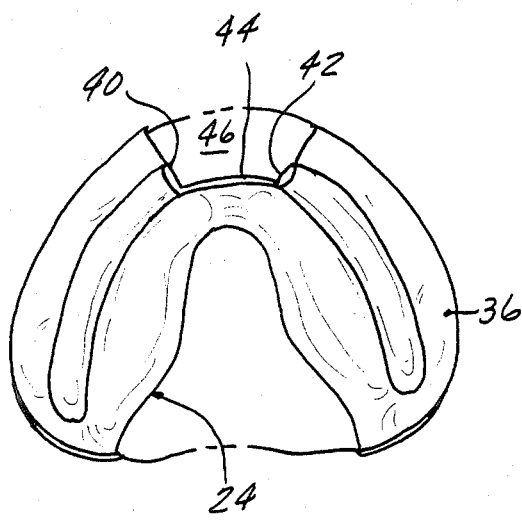
FIG. 7, is a plan view of the anterior relieved model of the stent according to the present invention.
Figure 8:
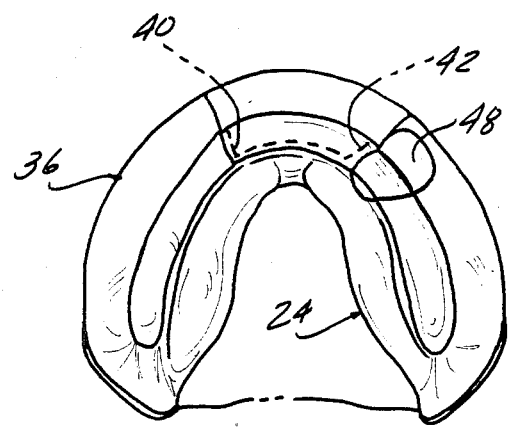
FIG. 8, is a plan view of a posterior relieved version of a stent according to the present invention.

A thin mix of number 2 plaster is then injected with syringe 33 into the ridge cavity of the stent 24, as shown in FIG. 6. After the plaster sets, a permanent or "master" model 36 is thereby produced, with the wax ridge 16 replaced with a more durable plaster ridge 38. The master model 36 may then be employed to vacuum form a number of stents 24 without danger of degradation of the shape of the specific ridge shape, contour, morphology, and design.

Implantation of the implant material requires vertical incisions to be made into the tissue, and the location of the incisions may be marked 40 and 42 on the permanent model 36. The stents 24 according to the present invention are used in conjunction with implantation stages in anterior and posterior ridge sections.

Accordingly, relieved versions of the stent 24 are provided, one used for each step. In the first version, the stent 24 is relieved by a "window" access opening in the anterior flange and cavity portion intermediate the points of incisions marked at 40 and 42, extending to the crest 44 of the section 26 ridge on the permanent model 36. Thus a midline access window opening 46 is formed in the stent 24.

The second version is used for implantation in the posterior ridge sections, and thus an access area 48 is created by a cutout in a section of the ridge section 26 immediately adjacent and distal to one of the lines of incision, either to the right or left depending on whether the placement is from the right or left, marked at 40 on the permanent master model 36. Reverification by implacement of the stent 24 on the permanent master model 36 should be done at this point.

The stent 24 having the relieved area 46 is positioned in the patient's mouth. Vertical incisions through the soft and periosteum tissues are made, and the soft and periosteum tissues subsequently surgically separated from the residual osseous ridge by means of a tunneling or similar surgical technique.

As noted, the wax which was removed from the temporary augmented model 18 is placed into a syringe that later will be utilized for comparision for injection of the implant material such that the volume of material in each section may be referenced by the implanting surgeon.

Subsequently, the relieved stents 24 are successively positioned in the patient's mouth. HA material is injected into the space between the separated tissues and osseous ridge for each anterior and posterior section, using the stents having relieved areas 46 and 48.

The overlying tissues are expanded by the injection of the implant material into engagement with the inside surface of the cavity section 26 of each stent 24. The transparency of the stents 24 allows the surgeon to observe when the proper fully expanded condition of each section of the tissue has been achieved.

An unrelieved stent 24 may then be employed to check the final ridge configuration, morphology, contour, and design.

A relatively soft material stent 24 may also be fabricated allowing adjustment of the final ridge morphology by manipulation through the correspondingly softer walls. All stents may be outlined to desired design extension.

As a final step, the unrelieved stent either soft or hard may be ligated into position for a period of weeks subsequent to the implant in order to maintain the position of the implant material during the bonding process to insure proper final intended pre operative ridge morphology and design.

Accordingly, it can be appreciated that the stents according to the present invention are very useful in alleviating the difficulties of using a granular or similar implant material, and insuring proper shaping and location of the augmented ridge.

While very useful in augmenting alveoler ridge morphology, the stents according to the present invention may be applied to other bone or implant augmentation situations such as maxillofacial defects, bone repair, etc.

Other implant material may also be employed such as alloplastic, homoplastic, and biogenic material, as well as other compositions suitable for these purposes.

I claim:

1. A surgical stent for implant augmentation to establish a tissuere morphology at a body site using a mass of implant material comprising:
    a member of transparent substantially rigid material having a cavity section forming an open sided cavity configured according to a desired tissue morphology, and having adjacent flange portions shaped to fit over the adjacent tissues and locate said open sided cavity in the position of said desired tissue morphology;
    said cavity section having at least one opening extending therethrough into said open sided cavity enabling access to the interior of said cavity for surgical procedures with said stent in position at said body site.

2. The stent according to claim 1 wherein said member extends in a general U-shape, whereby said stent is adapted to shape tissue morphology of the alveolar ridge.

3. The stent according to claim 2 wherein said opening is located at the midline of the anterior section of said member forming said open sided cavity.

4. The stent according to claim 2 wherein said opening is adjacent to the central anterior section of said member forming said open sided cavity.

5. The stent according to claim 1 wherein said member is formed of transparent plastic sheet material.

6. The stent according to claim 5 wherein said stent is formed of a hard polyacrylic approximately 0.08 inches thick.

7. A surgical stent for alveolar ridge augmentation, formed by a process of:
    forming a model of the existing ridge;
    constructing an augmented working model having a specific ridge morphology and design by adding material to said working model and shaping said added material to a specific ridge morphology and design to accept a prosthesis;
    molding a sheet of transparent material against said ridge portion of said augmented working model to form a cavity section configured as said desired ridge morphology;
    forming flange portions adjacent said cavity section, of said augmented model forming openings in a portion of said cavity section enabling access to said cavity for surgical procedures with said stent in position over said alveolar ridge.

8. The stent according to claim 7 wherein said molding step is carried out using material comprised of a soft plastic.

9. The stent according to claim 7 wherein said molding step material is carried out using a hard plastic material.

* * * * *